United States Patent [19]
Homsy

[11] 4,455,690
[45] Jun. 26, 1984

[54] STRUCTURE FOR IN VIVO IMPLANATION
[76] Inventor: Charles A. Homsy, 11526 Raintree Cir., Houston, Tex. 77024
[21] Appl. No.: 204,529
[22] Filed: Nov. 6, 1980
[51] Int. Cl.³ .............................................. A61F 1/00
[52] U.S. Cl. .................................................. 3/1; 3/1.9; 128/92 C
[58] Field of Search ..................... 3/1, 1.91; 128/92 C, 128/92 CA, 335 R

[56] References Cited
U.S. PATENT DOCUMENTS

| | | | |
|---|---|---|---|
| 3,797,047 | 3/1974 | Pillet | 3/1 |
| 3,805,300 | 4/1974 | Tascon-Alonso et al. | 3/1 |
| 3,882,551 | 5/1975 | Helmer et al. | 3/1 |
| 3,902,493 | 9/1975 | Baier et al. | 128/270 |
| 3,971,670 | 7/1976 | Homsy | 3/1 |
| 3,987,497 | 12/1976 | Stoy et al. | 3/1 |
| 3,992,725 | 11/1976 | Homsy | 3/1 |
| 4,187,558 | 12/1980 | Dahlen et al. | 3/1 |
| 4,246,660 | 1/1981 | Wevers | 3/1 |
| 4,304,010 | 12/1981 | Mano | 3/1 |

FOREIGN PATENT DOCUMENTS 260819  1/1970  U.S.S.R. ............................ 128/92 C

Primary Examiner—Richard J. Apley
Assistant Examiner—D. J. Isabella
Attorney, Agent, or Firm—Vinson & Elkins

[57] ABSTRACT

A structure suitable for in vivo implantation in a tension application having a plurality of longitudinal strands of a fabric with the ends of the strands in the fabric and bonded with a film, a sleeve surrounding the strands, the strands being slidable with respect to each other and movable in the sleeve for adjusting their relative positions whereby the structure load is substantially uniformly distributed among the strands and a means on the ends of the structure for securing the structure in implanted position.

35 Claims, 6 Drawing Figures

STRUCTURE FOR IN VIVO IMPLANATION

BACKGROUND

The present invention relates to an improved structure suitable for in vivo implantation as a tension member, such as a ligament or a tendon.

Some ligament and tendon damage is not repairable by surgery except by transplant or by the implantation of prepared structures. One requirement for such structures is that they should have extended fatigue resistance so that their replacement by surgery is not required during the normal patient life.

The problems of attachment of the ends of the implanted tension structure, of causing a tunnel to form to allow sliding movement of the implanted tension member and of biocompatibility have been solved by the structure disclosed in U.S. Pat. No. 4,127,902 (C. A. Homsy). However, increased fatigue resistance is advantageous in such implantable structures.

SUMMARY

The present invention provides an improved structural tension member including a film bonded on the ends of fabric which has a plurality of parallel strands extending between the film bonded ends, such strands having sufficient lubricity so as to slide relatively easily with respect to each other, the film bonded fabric ends and strands being formed into an elongate structure, a tubular sheath surrounding the central portion of the elongate element and bonded near at least one end to the film. Such structure allows each of the strands to carry a substantially equal share of the load independent of the flexing of the structure.

An object of the present invention is to provide an improved implantable tension structure which has improved flexural characteristics and fatigue resistance.

Another object is to provide an improved substitute ligament or tendon structure having potential for longer use when implanted in vivo.

A further object is to provide an improved structure for in vivo implantation which resist damage that might result from tissue contact.

BRIEF DESCRIPTION OF THE DRAWINGS

These and other objects and advantages of the present invention are hereinafter set forth and explained with reference to the drawings wherein.

DESCRIPTION OF THE PREFERRED EMBODIMENTS

Figure 1:
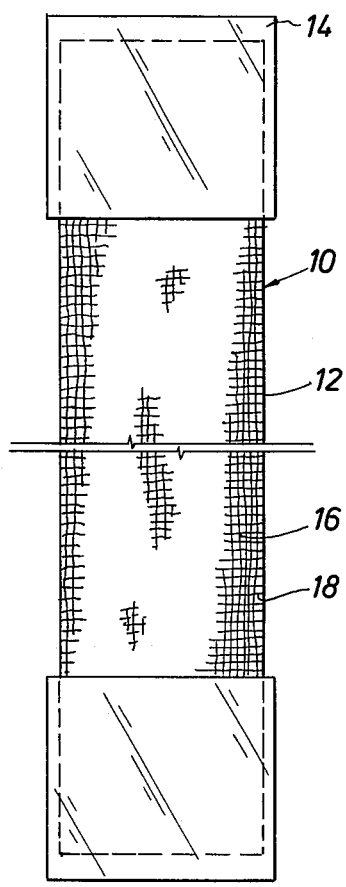
FIG. 1 is a layout view of the fabric and film laminate, before removal of the transverse strands and folding steps, used to form the cruciate ligament of the invention.

As shown in FIG. 1, structure 10 includes fabric 12 with films 14 suitably bonded on each end thereof. Fabric 12 and films 14 are biocompatible and fabric 12 is heat stable at the temperature used for the bonding of films 14 on the ends of fabric 12. Film 14 is preferred to be one of a perfluorocarbon, a perfluoroalkoxy fluorocarbon, a high molecular weight polyethylene, a hydrohalocarbon or a halocarbon.

The preferred material of fabric 12 is "Leno-weave" fabric of polyamide (nylon) material, such as polyaramide, sold by DuPont Company under the mark "Nomex". Such fabric is available from Stern & Stern, Inc. of Hornell, N.Y. as fabric type HT-63-30. Other fabrics suitable for the invention are polytetrafluoroethylene fabric, polyimide fabric and polyester fabric. In such fabric, the strands or fibers extending in one direction (longitudinal or warp strands 16) are disposed in twisted pairs and the fibers or strands extending in the perpendicular or transverse direction (fill strands 18) pass through the twisted pairs of the warp strands 16.

As used herein, the terms strand and fiber are used to mean the elements of the fabric and are not intended to exclude monofilaments.

Before the films 14 are bonded to the ends of fabric 12, fill strands 18 are removed from the end portions of fabric 12 which are to be covered by films 14 so that only warp strands 16 remain in the ends after bonding. This leaves a structure of a plurality of strands with their ends in the fabric and bonded by film 14.

Since it is desired that strands 16 be more easily slidable with respect to each other than they are initially, they are suitably coated with a biocompatible resin to improve their lubricity. This is accomplished by immersing strands 16 in a slurry of suitable polytetrafluoroethylene resin such as is available from DuPont Company under the mark Teflon T-6 in a suitable wetting liquid, such as isoparaffine solvent marketed by Exxon Chemical Company under the mark Isopar E. The slurry is prepared by adding 9.9 grams of the Teflon T-6 resin to 600 cc of Isopar E and blending for sufficient time (5 minutes) to develop an intimate dispersion. With the blender on, the strands are dipped into the slurry for a period of time sufficient to coat strands 16, as for example one-half minute to five minutes. Strands 16 are removed from the slurry and the solvent evaporated, for example, by drying in an oven for two hours. This procedure has been found to provide a substantially uniform coating of the strands with particles of the Teflon T-6 resin.

Figure 3:
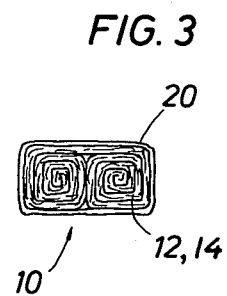
FIG. 3 is a sectional view of the structure taken along line 3—3 in FIG. 2.

Thereafter, the film coated ends and strands 16 are folded into compact rectangular shape as shown in FIG. 3.

A suitable tissue ingrowth material, such as porous coatings 20, are bonded to the ends of the structure. Other means may be used for securing the ends of the structure when it is implanted. Porous coatings 20 may be of the material as described in my prior U.S. Pat. No. 4,129,470.

The formed ends and strands are inserted in a sleeve 22 of porous, Teflon TFE polymer wherein the porosity of the sleeve is in the range from 50 to 90 percent pore volume and preferably 60 percent pore volume. The material of such sleeve is preferred to be the material described in my application for patent executed concurrently herewith, filed on Nov. 6, 1980 and assigned Ser. No. 204,528. Such material is a porous, fibrous structure of polytetrafluoroethylene fibers and resin.

Sleeve 22 is formed around a mandrel by heat and pressure in a sintering operation. The outer surface of sleeve 22 is modified in such sintering so that some of the resin melts and covers the outer surface to reduce its pore openings and thereby provide a surface which inhibits the ingrowth of tissue. When formed, the pore forming material is leached therefrom.

When maximum surface porosity is desired to enhance tissue ingrowth, as when this structure may be used for replacement of the collateral ligaments of the knee, the occluding resin skin can be removed by mild mechanical abrasion. Conversely the surface porosity can be totally obliterated, as is described below for the structure suitable for substitute for a tendon by coating the surface with medical grade silicone rubber. A suitable means is to dip or spray coat with a dispersion of medical grade silicone rubber in a non-polar vehicle such as Chlorthene halogenated ethylene solvent. It has been unexpectedly found that such thin coatings of silicone rubber are tenaciously bound to the surface of the sleeve. Since polytetrafluoroethylene is well known for its resistance to adhesion to other materials especially non-polar materials such as silicone rubber, the tenacity of attachment of the coating on the sleeve is surprising.

Furthermore, it has been found that vacuum impregnation of the entire porosity of the sleeve with said dispersion of silicone rubber followed by appropriate drying and curing of the rubber yields a novel composite of PTFE polymer and silicone rubber elastomer. This composite retains the flexibility of the porous PTFE sleeve material but exhibits enhanced resiliency, toughness and flexural fatigue behavior. By appropriate adjustment of the vacuum impregnation conditions the depth of impregnation of the silicone rubber into the porous PTFE sleeve material can be controlled and can produce a silicone coating more tenaciously bound than that achieved by the simple dipping or spraying procedures described above.

Sleeve 22 is positioned around the formed structure and the short length of each end, not less than 1 cm is bonded by heat to the film covered portion of the structure. Surface occlusion with silicone rubber may be carried out after this step.

Thus, a complete structure is formed suitable for implantation in vivo in substitute for a ligament. The strands 16 within sleeve 22 are free to move therein to adjust their positions so that with the flexural loading of the structure along this portion of the structure, stress is substantially uniformly distributed to the strands in all positions of flexion. Also, sleeve 22 protects strands 16 from abrasion or other damage by reason of engagement by or between tissue elements, such as bones, cartilage or soft tissue. One end of substitute ligament structure is formed in a reduced size to provide a leader 24 which eases the insertion of the end through a hole in a bone.

Figure 2:
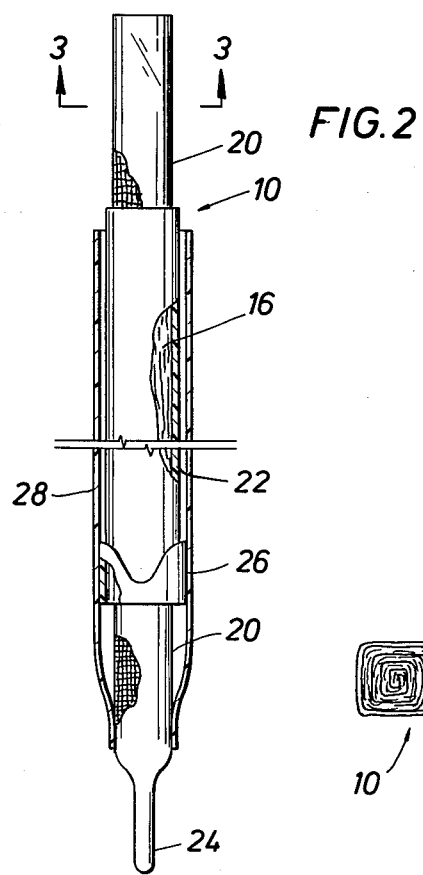
FIG. 2 is a plan view, partially cut away, of a preferred form of the cruciate ligament structure of the invention with portions broken away to show the interior structure.

As shown in FIG. 2, a means is provided on the ligament prosthesis to protect sleeve 22 from damage in the area where the structure enters or leaves a hole in bone. Such protection means is advisable since both ends of drilled holes or tunnels usually are not always available to the surgeon for rounding the entrances and exits to and from such tunnels. The preferred form of such protection means is skirt 26 of previously described polytetrafluoroethylene in the form of a tube four to five centimeters long with one to two centimeters at either end of skirt 26 being bonded to the exterior of sleeve 22 at either or both ends of sleeve 22 depending upon the mode of implantation. Skirt 26 may be shaped so that it does not totally encircle sleeve 22 along the free (unbonded) length as shown in FIG. 2 or may be a tube of uniform length.

An additional protection means is provided in the form of protective sheath 28 which is tubular in shape and is formed of Nomex fabric and PTFE film with the PTFE film overlapping but with a longitudinal gap between the Nomex fabric. Sheath 28 is secured around the portion of structure close to leader 24 and extends over a substantial portion of sleeve 22 so that it is protected in threading into its implanted position. Then leader 24 is cut from the positioned structure and the bonded portion of sheath 28 is removed with such cut and sheath 28 is easily cut longitudinally in that film portion which is free of fabric and removed from the implant structure and discarded.

Figure 4:
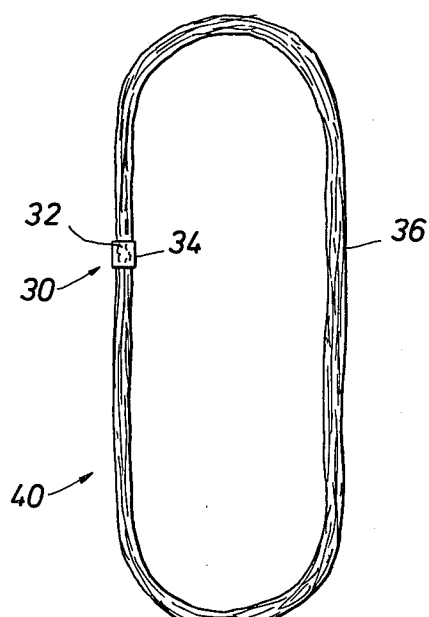
FIG. 4 is a view of the initial form of the tendon structure of FIG. 5, illustrating the longitudinal fibers in a loop.
Figure 6:
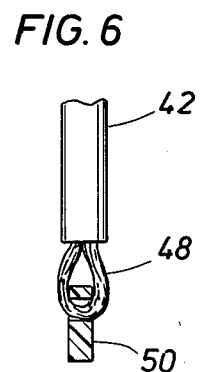
FIG. 6 is a partial view of the preferred tendon structure showing a means for attaching the tendon in its implanted position.
Figure 5:
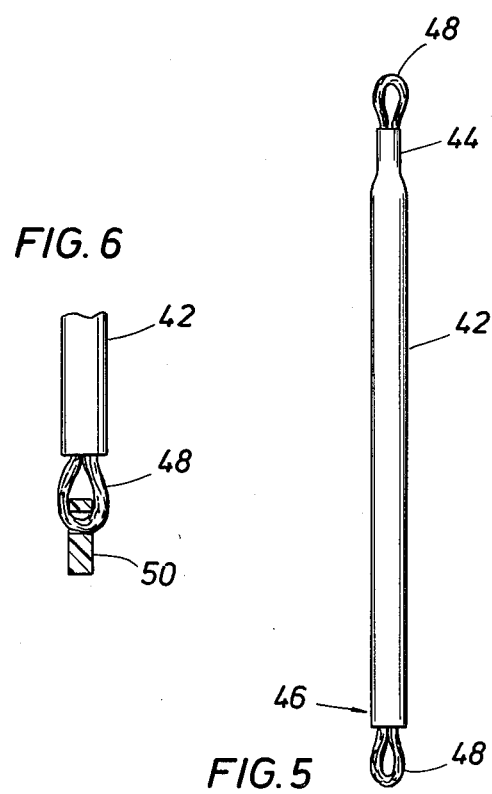
FIG. 5 is a view of the tendon structure of the invention.

A similar structure 30 suitable for in vivo implantation as a substitute tendon is shown in FIGS. 4, 5, and 6. Fabric 32 is similar to fabric 12. Teflon FEP film 34 is bonded to the ends of fabric 32 and then the two ends are bonded together to form the loop 40. The transverse strands of fabric 32 are removed either after film 34 is bonded to its ends or after loop 40 is formed to leave the longitudinal strands 36. Strands 36 are immersed in the Teflon T-6-Isopar-E slurry for coating as previously described. Loop 40 is inserted into tube 42 with fabric ends 32 and film 34 immediately within one end of tube 42. Such tubes are easily flexible and may be formed of non porous material such as silicone rubber or porous material having no external porosity or only small dimension exterior porosity not efficient for tissue ingrowth. Tube 42 is approximately three millimeters in diameter and of sufficient length for the particular tendon application. One end 44 of tube 42 is bonded to film 34 and fabric ends 32 by suitable heat and pressure or silicone adhesive. The other end 46 is sealed with a silicone rubber. Thus, entry of materials or tissue into the interior of the tube 42 is prevented.

Tube 42 may be made from the same material as the material of sleeve 22 previously described. However, for implantation of such material in a substitute tendon application, any pores in the outer surface of tube 42 are occluded by annealing in the sintering process or by coating with silicone rubber as previously described. This provides a surface which inhibits the ingrowth of tissue so that the substitute tendon is not prevented from free sliding movement in its implanted position. Tube 42 may also be a polytetrafluoroethylene vascular graft material sold by W. L. Gore and Associates of Flagstaff, Ariz. under the mark Gore-Tex. This material must also have external pores occluded by coating with silicone rubber as previously described or other suitable means.

Structure 30, as shown in FIG. 5, includes strands 36 extending from the ends of tube 42 in the form of loops 48. Ingrowth material 50 may be secured in one or both of loops 48 by silicone rubber as shown in FIG. 6. Ingrowth material 50 is preferred to be the porous material of graphite fibers bonded with tetrafluoroethylene as disclosed in my prior U.S. Pat. No. 3,992,725. A material of polyester fiber velour would also be suitable.

Thus, tendon replacement structure 30 has a plurality of strands 36 having sufficient lubricity to adjust their positions relative to each other and are contained within tube 42 which is sufficiently large and flexible to allow such position adjustment so that each strand carries substantially all of its share of the load in all positions of the implanted structure, reduces inter-fiber wear and the strands are protected from damage by rubbing against bone or being caught between bones and crushed.

It is preferred that the tube or sleeve in which the strands are positioned have an internal cross-sectional area which is approximately twice the cross-sectional area occupied by the strands so that the strands are not restricted from their desired position adjustment to assume their share of the load.

It is understood that all materials used in the improved tension structures are to be biocompatible.

What is claimed is:

1. A structure suitable for in vivo implantation in tension applications comprising
   a plurality of biocompatible strands,
   biocompatible means securing the ends of the strands,
   means coating the strand portion between said ends so that such strand portions have sufficient lubricity to be slidable with respect to each other,
   biocompatible protection means surrounding a substantial portion of said strands between their secured ends and coacting with the strands to allow spatial adjustment of their positions so that on flexing the strands move to the inside of the bend whereby each strand carries substantially all of its share of the structure loading in all positions of the implanted structure, and
   means on the ends of the strands for securing the structure in implanted position.

2. A structure according to claim 1 wherein said protection means includes
   a porous sleeve surrounding the insecured portions of said strands between said secured ends and being sufficiently flexible to allow the strands spatial adjustment of their positions.

3. A structure according to claim 2 including
   means on the outer surface of said sleeve which resists tissue ingrowth into the sleeve.

4. A structure according to claim 3 wherein
   the outer surface of said sleeve is modified to reduce the openings by resin melting therein.

5. A structure according to claim 3 wherein said sleeve includes silicone rubber filling its outer surface porosity.

6. A structure according to claim 3 wherein said sleeve has external pores which are impregnated with silicone rubber.

7. A structure according to claim 2 wherein said sleeve has an outer surface which promotes tissue ingrowth into the sleeve.

8. A structure according to claim 2 wherein said sleeve has a porosity within the range of 50 percent to 90 percent pore volume.

9. A structure according to claim 1 wherein said protection mans includes
   a silicone rubber sleeve surrounding the insecured portions of said strands between said secured ends and being sufficiently flexible to allow the strands spatial adjustment of their positions.

10. A structure according to claim 1 including
    a removable protective sheath surrounding a substantial portion of said protection means providing protection during emplacement of the structure.

11. A structure according to claim 1 including
    a protective skirt secured around a portion of said protection means to position said skirt at the entrance or exit of holes through bone.

12. A structure suitable for in vivo implantation comprising
    a biocompatible fabric,
    a biocompatible film being heat formed at a suitable heat forming temperature into at least a portion of said fabric,
    said fabric being heat stable at the heat forming temperature of said film,
    said fabric having a weave consisting of fibers extending in a longitudinal direction, which are disposed in twisted pairs, and fibers extending in a transverse direction, which pass through said twisted pairs,
    said transverse fibers being removed from said fabric which is not heat formed with said film,
    means coating said longitudinal fibers with a biocompatible resin to provide lubricity to said longitudinal fibers to allow spatial adjustment of their positions so that on flexing the strands move to the inside of the bend whereby each strand carries substantially all of its share of the structure loading in all positions of the implanted structure, and
    a protective tubular sleeve covering said longitudinal fibers.

13. The structure of claim 12, wherein said biocompatible resin which coats said longitudinal fibers is polytetrafluoroethylene.

14. The structure of claim 12, wherein said heat formed fabric and film with longitudinal strands extending therefrom is folded a plurality of times to form an elongate structure with bonded ends and longitudinal strands therebetween.

15. A substitute ligament comprising
    a biocompatible fabric,
    a biocompatible film being heat formed at a suitable heat forming temperature into at least a portion of said fabric,
    said fabric being heat stable at the heat forming temperature of said film,
    said fabric having a weave consisting of fibers extending in a longitudinal direction, which are disposed in twisted pairs, and fibers extending in a transverse direction, which pass through said twisted pairs,
    said transverse fibers being removed from said fabric which is not heat formed with said film,
    said longitudinal fibers being coated with polytetrafluoroethylene resin to provide lubricity to said longitudinal fibers, and
    a protective tubular sleeve covering said longitudinal fibers,
    said heat formed fabric and film with longitudinal strands extending therefrom is folded a plurality of times to form an elongate structure with bonded ends and longitudinal strands therebetween.

16. The structure of claim 12, wherein said protective tubular sleeve has a porosity within the range of 50 percent to 90 percent pore volume.

17. The structure of claim 12, wherein said protective tubular sleeve has a porosity of about 60 percent pore volume and wherein the pores of outer skin of said sleeve are substantially closed to provide a surface that prevents ingrowth of surrounding tissue when said structure is implanted.

18. The structure according to claim 17 wherein
    the pores in the outer skin of said sleeve are closed with silicone rubber.

19. The structure of claim 12, wherein said protective tubular sleeve has a porosity of about 60 percent pore volume, and wherein a minor portion of said pore volume resides in the exterior portion of said tubular sleeve.

20. A structure suitable for in vivo implantation comprising
   a biocompatible fabric,
   a biocompatible film being heat formed at a suitable heating forming temperature into at least a portion of said fabric,
   said fabric being heat stable at the heat forming temperature of said film,
   said fabric having a weave consisting of fibers extending in a longitudinal direction, which are disposed in twisted pairs, and fibers extending in a transverse direction, which pass through said twisted pairs,
   said transverse fibers being removed from said fabric which is not heat formed with said film,
   said fabric being folded a plurality of times to form an elongate structure wherein said heat formed film and fabric is positioned on each end of said implantable structure and wherein there is an intermediate portion of said structure not formed with said film and from which the transverse fibers have been removed,
   means coating said intermediate portion of said structure with biocompatible resin particles to provide lubricity to said longitudinal fibers to allow spatial adjustment of their positions so that on flexing the strands move to the inside of the bend whereby each strand carries substantially all of its share of the structure loading in all positions of the implanted structure, and
   a porous, protective tubular sleeve positioned over and essentially completely encapsulating said resin particle coated intermediate portion of said structure.

21. The structure of claim 20, wherein said tubular sleeve comprises a polytetrafluoroethylene treated to have a porosity of about 50 percent to about 90 percent pore volume, and wherein the outer surface area of said tubular sleeve resists ingrowth of surrounding tissue when said structure is implanted.

22. The structure of claim 21, wherein said tubular sleeve has a minor portion of said pore volume residing in the exterior portion thereof.

23. The structure of claim 20, wherein said protective tubular sleeve has a porosity of about 60 percent pore volume.

24. The structure of claim 21 wherein silicone rubber is bonded to the exterior of said tubular sleeve.

25. The structure of claim 20 wherein said tubular sleeve is silicone rubber.

26. The structure of claim 20, wherein said biocompatible fabric is selected from the group consisting of a polyamide fabric, a polytetrafluoroethylene fabric and a polyester fabric, and
   said film is selected from the group consisting of a perfluorocarbon, a perfluoroalkoxy fluorocarbon, a high molecular weight polyethylene, a hydrohalocarbon and a halocarbon.

27. The structure of claim 20, wherein there is secured to at least a portion of the folded fiber and film portions of said structure a biocompatible porous material which promotes ingrowth of living tissue within its pores.

28. The structure of claim 27 wherein said porous material is a porous material of graphite fibers bonded with a polytetrafluoroethylene.

29. The structure of claim 27, wherein said porous material is a polyester fiber velour material.

30. The structure of claim 20, wherein said biocompatible resin particles comprises polytetrafluoroethylene.

31. A structure suitable for in vivo implantation comprising
   a biocompatible fabric,
   a biocompatible film being heat formed at a suitable heat forming temperature into a minor portion of said fabric,
   said fabric being heat stable at the heat forming temperature of said film,
   a major portion of said fabric, not heat formed with said film, comprising longitudinally extending fibers disposed in twisted pairs with no transverse fibers,
   means coating the portion of the longitudinal fibers with no transverse fibers with resin particles to increase the lubricity of the longitudinal fibers to allow spatial adjustment of their positions so that on flexing the strands move to the inside of the bend whereby each strand carries substantially all of its share of the structure loading in all positions of the implanted structure,
   said fabric being an elongated loop configuration and having a protective sleeve encapsulating a major portion of the elongated loop, said sleeve comprising a biocompatible, semi-porous material which is resistant to ingrowth of living tissue, and
   means on each end of said elongate loop for providing a site for attachment to tissue.

32. A substitute tendon comprising
   a biocompatible fabric,
   a biocompatible film being heat formed at a suitable heat forming temperature into a minor portion of said fabric,
   said fabric being heat stable at the heat forming temperature of said film,
   a major portion of said fabric, not heat formed with said film, comprising longitudinally extending fibers disposed in twisted pairs and with no transverse fibers,
   means coating the portion of the longitudinal fibers having no transverse fibers with resin particles to increase the lubricity of the longitudinal fibers to allow spatial adjustment of their positions so that on flexing the strands move to the inside of the bend whereby each strand carries substantially all of its share of the structure loading in all positions of the implanted structure,
   said fabric being an elongated loop configuration and having a protective sleeve encapsulating a major portion of the elongated loop,
   said sleeve comprising a biocompatible, semi-porous material which is resistant to ingrowth of living tissue, and
   means on each end of said elongate loop for providing a site for attachment to tissue.

33. The structure of claim 31, wherein said longitudinal fibers of said fabric, encapsulated within said sleeve have coated thereon a biocompatible resin.

34. The structure of claim 31, wherein said tubular sleeve is polytetrafluoroethylene having a porosity of about 50 percent to about 90 percent pore volume, and wherein the outer surface area of said tubular sleeve resists ingrowth of surrounding living tissue.

35. The structure of claim 31, wherein said biocompatible fabric is selected from the group consisting of a polyamide fabric, a polyimide fabric, a polytetrafluoroethylene fabric and a polyester fabric.

* * * * *